United States Patent
Li et al.

(10) Patent No.: US 12,269,998 B2
(45) Date of Patent: Apr. 8, 2025

(54) METHOD AND SYSTEM FOR PROCESSING GASOLINE FRACTIONS

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Jingqiu Li, Shanghai (CN); Dejin Kong, Shanghai (CN); Xuguang Li, Shanghai (CN); Zongshuang Wang, Shanghai (CN); Huaying Li, Shanghai (CN); Weiyi Tong, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 99 days.

(21) Appl. No.: 18/249,962

(22) PCT Filed: Oct. 22, 2021

(86) PCT No.: PCT/CN2021/125584
§ 371 (c)(1),
(2) Date: Apr. 20, 2023

(87) PCT Pub. No.: WO2022/082372
PCT Pub. Date: Apr. 28, 2022

(65) Prior Publication Data
US 2023/0407193 A1 Dec. 21, 2023

(30) Foreign Application Priority Data

Oct. 22, 2020 (CN) .......................... 202011138771.9

(51) Int. Cl.
*C10G 63/04* (2006.01)
*B01J 29/48* (2006.01)
*B01J 29/40* (2006.01)

(52) U.S. Cl.
CPC .............. *C10G 63/04* (2013.01); *B01J 29/48* (2013.01); *B01J 29/405* (2013.01);
(Continued)

(58) Field of Classification Search
CPC ......... B01J 29/405; B01J 29/48; C07C 15/08; C07C 6/12; C10G 2300/1037;
(Continued)

(56) References Cited

U.S. PATENT DOCUMENTS 3,729,409 A 4/1973 Chen
2008/0026931 A1 1/2008 Boldingh et al.
(Continued)

FOREIGN PATENT DOCUMENTS

CN 1122571 C 10/2003
CN 1485414 A 3/2004
(Continued)

*Primary Examiner* — Ellen M McAvoy
*Assistant Examiner* — Chantel Graham
(74) *Attorney, Agent, or Firm* — NKL Law; Allen Xue

(57) ABSTRACT

A method for processing a gasoline fraction includes the steps of: a) reacting the gasoline fraction in an aromatization unit, and separating the resulting reaction product to obtain a $C_4^-$ component, a $C_5$ component, a $C_6$-$C_7$ component, a $C_8$ component and a $C_9^+$ component; b) reacting the resulting $C_6$-$C_7$ component and the $C_9^+$ component in a cracking and aromatics conversion unit, and separating the resulting reaction product to obtain a $C_4^-$ component, a $C_5$ component, a $C_6$-$C_7$ component, a $C_8$ component and a $C_9^+$ component;

(Continued)

and c) recycling at least a part of at least one of the $C_6$-$C_7$ component and the $C_9^+$ component from step b) to the cracking and aromatics conversion unit of step b) for further reaction. The method can convert the gasoline fraction into $C_8$ aromatic hydrocarbon(s) and produce light olefins and a high-quality light gasoline as byproducts.

16 Claims, 4 Drawing Sheets

(52) U.S. Cl.
CPC ............... *C10G 2300/1037* (2013.01); *C10G 2300/4006* (2013.01); *C10G 2300/4012* (2013.01); *C10G 2300/4018* (2013.01); *C10G 2300/4081* (2013.01); *C10G 2300/70* (2013.01); *C10G 2400/02* (2013.01); *C10G 2400/20* (2013.01); *C10G 2400/30* (2013.01)

(58) Field of Classification Search
CPC .... C10G 2300/4006; C10G 2300/4012; C10G 2300/4018; C10G 2300/4081; C10G 2300/70; C10G 2400/02; C10G 2400/20; C10G 2400/30; C10G 35/095; C10G 63/04; C10G 47/16; C10G 57/00; Y02P 20/52

See application file for complete search history.

(56) References Cited

U.S. PATENT DOCUMENTS

| 2015/0321976 A1 | 11/2015 | Larson et al. |
| 2015/0376086 A1 | 12/2015 | Tinger et al. |
| 2020/0017773 A1 | 1/2020 | Ramamurthy et al. |

FOREIGN PATENT DOCUMENTS

| CN | 1923965 A | 3/2007 | |
| CN | 101734986 A | 6/2010 | |
| CN | 101880213 A | 11/2010 | |
| CN | 103261124 A | 8/2013 | |
| CN | 103772123 A | 5/2014 | |
| CN | 107285976 A | 10/2017 | |
| CN | 110938464 A | 3/2020 | |
| EP | 3015445 A1 | 5/2016 | |
| WO | WO-9905081 A1 * | 2/1999 | ............. C10G 61/00 |

* cited by examiner

METHOD AND SYSTEM FOR PROCESSING GASOLINE FRACTIONS

CROSS REFERENCE TO RELATED APPLICATIONS

The present application is a national entry of International Application No. PCT/CN2021/125584 filed on Oct. 22, 2021, which claims the benefit of priority to the Chinese patent application No. 202011138771.9, titled "system and method for processing gasoline fractions", filed on Oct. 22, 2020, the contents of which are incorporated herein by reference in their entirety.

TECHNICAL FIELD

The present application relates to the processing of hydrocarbons, particularly to a method and system for processing gasoline fractions.

BACKGROUND ART

Aromatic hydrocarbons are basic raw materials of petrochemical industry, para-xylene is a main aromatic hydrocarbon product, the supply gap of the para-xylene in China reaches more than 1000 million tons per year in recent years, and the acceleration of the development of aromatic hydrocarbon industry is vital to the development of the basic chemical industry in China. In industrial plants, aromatic hydrocarbons are mainly produced through catalytic reforming process using naphtha as a raw material, and then toluene/benzene and $C_9^+A$ are converted into xylene through an isomerization and transalkylation unit. In addition, the steam cracking device for producing light olefins in China also mainly takes naphtha as a raw material, so that the raw materials for producing aromatics and olefins compete with each other, and the cost of the aromatics and olefins raw materials is high. Therefore, the search for lower cost and diversified raw materials for producing aromatics and olefins is a key factor for solving the problem encountered in the development of aromatics and olefins industries in the future.

With the application and popularization of new energy technology and the upgrading of gasoline in China, the demand of gasoline for vehicles tends to decline in the future, and the contradiction of oversupply will appear in the gasoline market. Therefore, the directional conversion of a part of inferior gasoline into high-value $C_8$ aromatic hydrocarbons is an effective way for widening the utilization of gasoline, and can relieve the shortage of raw material for producing para-xylene.

CN1923965 discloses a method for producing ethylene, propylene and aromatic hydrocarbons from catalytic cracking gasoline, wherein a raw material is contacted with a catalyst once for conversion into a mixture of ethylene, propylene and aromatic hydrocarbons.

The conversion of a hydrocarbon raw material comprising non-aromatic hydrocarbons into aromatic hydrocarbons is mainly realized by aromatization technology, in which light olefins and alkanes are used for producing aromatic hydrocarbons through a complex aromatization process, so that the diversification of aromatics production raw materials can be realized. The product distribution of said process is closely related to the structure of the raw material, and main products include benzene, toluene, $C_8$ aromatic hydrocarbons, heavy aromatic hydrocarbons and non-aromatic hydrocarbon components. Therefore, directional increase of the production of high-purity C8 aromatic hydrocarbons is difficult to be realized by aromatization technology alone. Benzene, toluene and heavy aromatics can be maximally converted into C8 aromatic hydrocarbons by aromatics transalkylation technology, and meanwhile, some light hydrocarbons can be produced as a byproduct. For example, CN1122571 discloses a noble metal-containing molecular sieve catalyst, which comprises 10-80 wt % of mordenite or β molecular sieve and 0-70 wt % of ZSM-5 and 5-90 wt % of γ-$Al_2O_3$ as a carrier, and 0.001-0.5 parts by weight of platinum and 0.01-10.0 parts by weight of tin or 0.01-7.0 parts by weight of lead supported on the carrier.

US2008/0026931A1 discloses a catalyst comprising an acidic molecular sieve and a metal component of rhenium, tin and germanium, which is used for transalkylation of heavy aromatics, and has a relatveily higher activity and a relatively lower loss rate of rings.

In the process for producing aromatic hydrocarbons as a target product, it is vital to obtain a high-purity product, aromatics plants mainly involve the separation of aromatic hydrocarbons from non-aromatic hydrocarbons through an extraction or rectification process, and the decomposition of non-aromatic hydrocarbons into small-molecule light hydrocarbons through a chemical cracking process, so that the purity of aromatic product can be improved.

U.S. Pat. No. 3,729,409 proposes to convert non-aromatic hydrocarbons mixed with aromatic hydrocarbons into lower alkanes via hydrocracking reaction in the presence of a catalyst, in which aromatic hydrocarbons can be separated from non-aromatic hydrocarbons using a vapor-liquid separator.

However, existing methods still have the problems of low comprehensive utilization of gasoline fractions and low product value.

SUMMARY OF THE INVENTION

An object of the present application is to provide a novel method and system for processing gasoline fractions, which can effectively expand the reaw materials for the production of aromatics and olefins and realize efficient comprehensive utilization of gasoline fractions.

To achieve the above object, in one aspect, the present application provides a method for processing a gasoline fraction, comprising the steps of:

I) reacting the gasoline fraction in an aromatization unit and separating the resulting reaction product to obtain a $C_4^-$ component, a $C_5$ component, a $C_6$-$C_7$ component, a $C_8$ component and a $C_9^+$ component, wherein the reaction occuring in the aromatization unit includes aromatization reaction;

II) reacting the $C_6$-$C_7$ component and the $C_9^+$ component from step I) in a cracking and aromatics conversion unit, and separating the resulting reaction product to obtain a $C_4^-$ component, a $C_5$ component, a $C_6$-$C_7$ component, a $C_8$ component and a $C_9^+$ component, wherein the reaction occuring in the cracking and aromatics conversion unit includes non-aromatics cracking reaction and transalkylation reaction;

III) optionally, purifying at least one of the $C_8$ components from steps I) and II), and separating the resultant to obtain a $C_4^-$ component, a $C_5$ component, a $C_6$-$C_7$ component, $C_8$ aromatic hydrocarbon(s) and a $C_9^+$ component;

IV) optionally, subjecting at least a part of at least one of the $C_4^-$ components from steps I), II), and III) to steam cracking or dehydrogenation reaction;

V) optionally, using at least a part of at least one of the $C_5$ components from steps I), II), and III) for gasoline blending; and VI) recycling the $C_6$-$C_7$ component and the $C_9^+$ component from step II), and at least a part of at least one of the $C_6$-$C_7$ component and the $C_9^+$ component from step III) to the cracking and aromatics conversion unit of step II) for further reaction.

In another aspect, the present application provides a method for processing a gasoline fraction, comprising the steps of:

1) reacting the gasoline fraction in the presence of an aromatization catalyst, and separating the resulting reaction product to obtain a $C_4^-$ component, a $C_5$ component, a $C_6$-$C_7$ component, $C_8$ component and a $C_9^+$ component;

2) reacting the $C_6$-$C_7$ component and the $C_9^+$ component from step 1) in the presence of an aromatics conversion catalyst, and separating the resulting reaction product to obtain a $C_4^-$ component, a $C_5$ component, a $C_6$-$C_7$ component, a $C_8$ component and a $C_9^+$ component;

3) optionally, purifying at least one of the $C_8$ components from steps 1) and 2), and separating the resultant to obtain a $C_4^-$ component, a $C_5$ component, a $C_6$-$C_7$ component, $C_8$ aromatic hydrocarbon(s) and a $C_9^+$ component;

4) optionally, subjecting at least a part of at least one of the $C_4^-$ components from steps 1), 2), and 3) to steam cracking or dehydrogenation reaction;

5) optionally, using at least a part of at least one of the $C_5$ components from steps 1), 2), and 3) for gasoline blending; and 6) recycling the $C_6$-$C_7$ component and the $C_9^+$ component from step 2), and at least a part of at least one of the $C_6$-$C_7$ component and the $C_9^+$ component from step 3), for further reaction in the presence of the aromatics conversion catalyst in step 2).

In yet another aspect, the present application provides a system for carrying out the gasoline fraction processing method of the present application, comprising:

an aromatization unit for reacting the gasoline fraction therein and separating the resulting reaction product to obtain a $C_4^-$ component, a $C_5$ component, a $C_6$-$C_7$ component, a $C_8$ component and a $C_9^+$ component;

a cracking and aromatics conversion unit for reacting the $C_6$-$C_7$ component and the $C_9^+$ component from the aromatization unit and separating the resulting reaction product to obtain a $C_4^-$ component, a $C_5$ component, a $C_6$-$C_7$ component, a $C_8$ component and a $C_9^+$ component;

optionally, an aromatics purification unit for purifying at least one of the $C_8$ components from the aromatization unit and the cracking and aromatics conversion unit and separating the resultant to obtain a $C_4^-$ component, $C_5$ component, a $C_6$-$C_7$ component, $C_8$ aromatic hydrocarbon(s) and a $C_9^+$ component;

optionally, a light hydrocarbon conversion unit for conducting steam cracking or dehydrogenation reaction on at least a part of at least one of the $C_4^-$ components from the aromatization unit, the cracking and aromatics conversion unit, and the optional aromatics purification unit; and optionally, a light gasoline blending unit for gasoline blending using at least a part of at least one of the $C_5$ components from the aromatization unit, the cracking and aromatics conversion unit, and the optional aromatics purification unit.

In the method and system according to the present application, a gasoline fraction comprising non-aromatic hydrocarbons is passed through the aromatization unit to increase the yield of mixed aromatic hydrocarbon product and meanwhile generate a non-aromatic hydrocarbon component with low olefin content and high isoparaffin content as a by-product; the $C_6$-$C_7$ component and $C_9^+$ component depleted in $C_8$ aromatic hydrocarbons are passed through the cracking and aromatics conversion unit to directionally convert benzene, toluene and $C_9^+$ aromatic hydrocarbons in those components into $C_8$ aromatic hydrocarbon(s), and meanwhile, non-aromatic hydrocarbons are slightly cracked into light hydrocarbons. Optionally, the $C_8$ aromatic hydrocarbon product is further purified in the aromatics purification unit to obtain high-purity $C_8$ aromatic hydrocarbon(s). The resulting by-product $C_4$ and lower hydrocarbons can be used as a high-quality raw material for steam cracking or dehydrogenation reaction, and the resulting by-product $C_5$ component has the characteristics of low olefin content and high isoparaffin content, and can be used as a high-quality gasoline blending material. This process can effectively and directionally convert gasoline fractions (such as catalytic gasoline fractions and LPG) into $C_8$ aromatic hydrocarbon(s), and produce light olefins and high-quality light gasoline as byproducts, thereby realizing an efficient comprehensive utilization.

By using the method according to the present application, the aromatics content in the reaction product of the aromatization unit is increased by 15% or more, preferably 25% or more, compared with the raw material; the $C_8$ aromatics content in the product of the cracking and aromatics conversion unit is increased by 20% or more, preferably 25% or more, compared with the raw material. Optionally, the aromatics purification unit is an extraction separation unit or a non-aromatics selective cracking unit, and the purity of the $C_8$ aromatic hydrocarbon product of the aromatics purification unit can reach 99% or higher.

Other characteristics and advantages of the present application will be described in detail in the detailed description hereinbelow.

BRIEF DESCRIPTION OF THE DRAWINGS

The drawings, forming a part of the present description, are provided to help the understanding of the present application, and should not be considered to be limiting. The present application can be interpreted with reference to the drawings in combination with the detailed description hereinbelow. In the drawings.

DETAILED DESCRIPTION OF THE INVENTION

Figure 1:
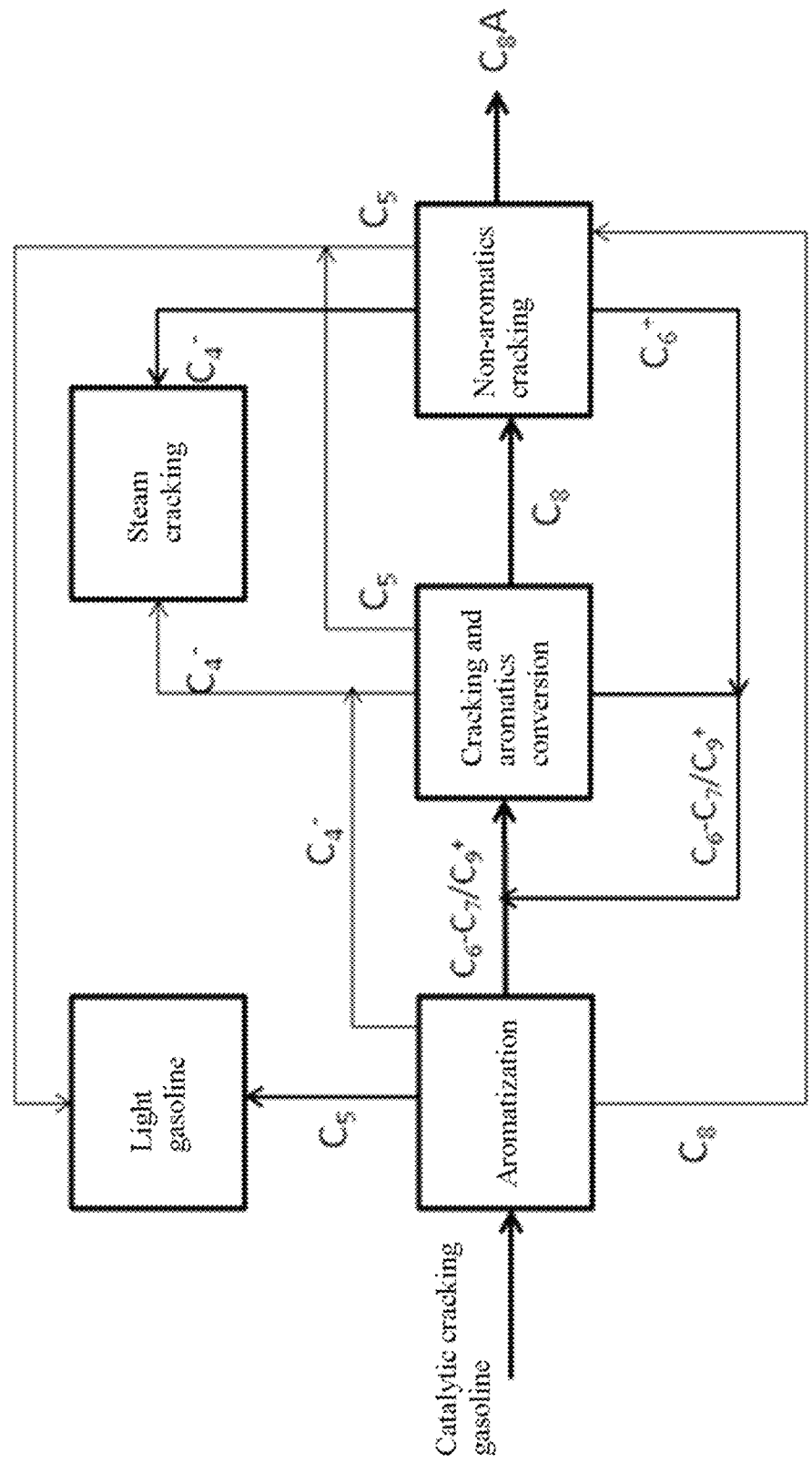
FIG. 1 is a schematic flow diagram of a preferred embodiment of the method according to the present application.

The present application will be further described hereinafter in detail with reference to the drawing and specific embodiments thereof. It should be noted that the specific embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value, for example all values within ±5% of said exact value. Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

Unless otherwise stated, the terms used herein have the same meaning as commonly understood by those skilled in the art; and if the terms are defined herein and their definitions are different from the ordinary understanding in the art, the definition provided herein shall prevail.

In the context of the present application, the term "gasoline fraction" refers to a fraction having a boiling range within that of gasoline (typically 30-205° C.), which includes, but is not limited to, catalytic cracking gasoline, hydrocracking gasoline, ethylene cracking gasoline, catalytic reformate, straight-run gasoline, LPG, any mixtures thereof, or a partial fraction thereof.

In the context of the present application, the $C_4^-$ component refers to a hydrocarbon component having a boiling point lower than 30° C.; the $C_5$ component refers to a hydrocarbon component having a boiling point in the range of 30° C. to lower than 70° C.; the $C_6$-$C_7$ component refers to a hydrocarbon component having a boiling point in the range of 70° C. to lower than 130° C.; the $C_8$ component refers to a hydrocarbon component having a boiling point in the range of 130° C. to 145° C.; and the $C_9^+$ component refers to a hydrocarbon component having a boiling point higher than 145° C.

In the context of the present application, high-purity $C_8$ aromatic hydrocarbon(s) refers to $C_8$ aromatic hydrocarbon(s) that meet the purity requirement for adsorptive separation or crystallization separation of para-xylene, which requirement is, for example, greater than 99%.

In the context of the present application, the term "acidic molecular sieve" has the meaning commonly understood in the art and refers to a molecular sieve having B acid and/or L acid sites.

In the present application, the medium strong acid content of the catalyst is calculated according to the peak area within a temperature range of 200-400° C. of its $NH_3$-TPD pattern; the ratio of the medium strong acid content to the total acid content refers to the ratio of the peak area within a temperature range of 200-400° C. to the total peak area within a temperature range of 100-600° C. of the $NH_3$-TPD pattern.

In the context of the present application, unless otherwise indicated, all pressures given are gauge pressures.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to the person skilled in the art that such a combination is obviously unreasonable.

All of the patent and non-patent documents cited herein, including but not limited to textbooks and journal articles, are hereby incorporated by reference in their entirety.

As described above, in a first aspect, the present application provides a method for processing a gasoline fraction, comprising the steps of:

I) reacting the gasoline fraction in an aromatization unit and separating the resulting reaction product to obtain a $C_4^-$ component, a $C_5$ component, a $C_6$-$C_7$ component, a $C_8$ component and a $C_9^+$ component, wherein the reaction occuring in the aromatization unit includes aromatization reaction;

II) reacting the $C_6$-$C_7$ component and the $C_9^+$ component from step I) in a cracking and aromatics conversion unit, and separating the resulting reaction product to obtain a $C_4^-$ component, a $C_5$ component, a $C_6$-$C_7$ component, a $C_8$ component and a $C_9^+$ component, wherein the reaction occuring in the cracking and aromatics conversion unit includes non-aromatics cracking reaction and transalkylation reaction;

III) optionally, purifying at least one of the $C_8$ components from steps I) and II), and separating the resultant to obtain a $C_4^-$ component, a $C_5$ component, a $C_6$-$C_7$ component, $C_8$ aromatic hydrocarbon(s) and a $C_9^+$ component;

IV) optionally, subjecting at least a part of at least one of the $C_4^-$ components from steps I), II), and III) to steam cracking or dehydrogenation reaction;

V) optionally, using at least a part of at least one of the $C_5$ components from steps I), II), and III) for gasoline blending; and VI) recycling the $C_6$-$C_7$ component and the $C_9^+$ component from step II), and optionally at least a part of at least one of the $C_6$-$C_7$ component and the $C_9^+$ component from step III), to the cracking and aromatics conversion unit of step II) for further reaction.

In a second aspect, the present application provides a method for processing a gasoline fraction, comprising the steps of:

1) reacting the gasoline fraction in the presence of an aromatization catalyst, and separating the resulting reaction product to obtain a $C_4^-$ component, a $C_5$ component, a $C_6$-$C_7$ component, a $C_8$ component and a $C_9^+$ component;

2) reacting the $C_6$-$C_7$ component and the $C_9^+$ component from step 1) in the presence of an aromatics conversion catalyst, and separating the resulting reaction product to obtain a $C_4^-$ component, a $C_5$ component, a $C_6$-$C_7$ component, a $C_8$ component and a $C_9^+$ component;

3) optionally, purifying at least one of the $C_8$ components from steps 1) and 2), and separating the resultant to obtain a $C_4^-$ component, a $C_5$ component, a $C_6$-$C_7$ component, $C_8$ aromatic hydrocarbon(s) and a $C_9^+$ component;

4) optionally, subjecting at least a part of at least one of the $C_4^-$ components from steps 1), 2), and 3) to steam cracking or dehydrogenation reaction;

5) optionally, using at least a part of at least one of the $C_5$ components from steps 1), 2), and 3) for gasoline blending; and 6) recycling the $C_6$-$C_7$ component and the $C_9^+$ component from step 2), and optionally at least a part of at least one of the $C_6$-$C_7$ component and the $C_9^+$ component from step 3), for further reaction in the presence of the aromatics conversion catalyst in step 2).

According to the present application, the separation of components in step I)/step 1), step II)/step 2) and step III)/step 3) is carried out by separating hydrocarbon-containing mixtures into components having different boiling points or boiling ranges through distillation, rectification or fractionation according to their boiling points. The specific operations and conditions used can be easily determined by those skilled in the art in view of the targeted component to be separated, of which the detailed description is omitted herein for brevity.

In a preferred embodiment, the gasoline fraction used in step I) and step 1) has one or more of the following characteristics:
a boiling range of 40-250° C., and a preferred boiling range of 50-200° C.;
an aromatics content of 10-100 wt %, preferably 20-80 wt %, more preferably 20-35 wt %;
a sulfur content of 2-4 ppm by weight;
a nitrogen content of 0.5-2 ppm by weight;
an olefin content of 20-40 wt %; and
an alkane content of 40-45 wt %.

In a preferred embodiment, the gasoline fraction used in step I) and step 1) is selected from the group consisting of catalytic cracking gasoline, hydrocracking gasoline, ethylene cracking gasoline, catalytic reformate, straight-run gasoline, LPG or any mixtures thereof, or a partial fraction thereof.

The gasoline fraction according to the above preferred embodiment can be more efficiently utilized by processing with the method according to the present application.

In the present application, the aromatization catalyst used in the aromatization unit of step I) and the aromatization catalyst used in step 1) may be those conventionally used, for example, may comprise 50 to 90 wt % of a molecular sieve selected from aluminosilicates, aluminogallosilicates, aluminosilicophosphates, aluminoferrosilicates and the like having a ten- or twelve-membered ring pore structure, and 0.5 to 10 wt % of a modifying metal (calculated as metal). The modifying metal is selected from Group IB, Group IIB, Group VIB, Group VIIB and Group VIII metals, and is preferably selected from Zn, Mo, Ga and Pt. Preferably, the molecular sieve used in the aromatization catalyst is ZSM-5, and the modifying metal is Zn and Ga.

In a preferred embodiment, the reaction conditions of step I) and step 1) include: a reaction temperature of 400-600° C., a reaction pressure of 0.2-3 MPa, and a feeding space velocity of 0.5-5 h$^{-1}$.

In the present application, the aromatics conversion catalyst used in the cracking and aromatics conversion unit of step II) and the aromatics conversion catalyst used in step 1) may be those conventionally used, for example, may comprise 50 to 90 wt % of a molecular sieve selected from aluminosilicates, and silicoaluminophosphates having an eight-, ten- or twelve-membered ring pore structure, preferably selected from ZSM-5 molecular sieves, ZSM-12 molecular sieves, MOR molecular sieves, and β molecular sieves, and 0.05 to 10 wt % of a modifying metal. The modifying metal component is selected from the group consisting of Group VB metals, Group VIB metals, Group VIIB metals, Group VIII metals and metal oxides thereof.

In a preferred embodiment, the aromatics conversion catalyst comprises an acidic molecular sieve component, an oxide additive, a first metal component (which may be in the form of metal and/or metal oxide), and a second metal component (which may be in the form of metal and/or metal oxide), wherein the first metal of the first metal component is one or more selected from the group consisting of Group VB metals, Group VIB metals, and Group VIIB metals, the second metal of the second metal component is a metal different from the first metal, the first metal component is immobilized on the acidic molecular sieve component, and the catalyst has a medium strong acid content of 0.05 to 2.0 mmol/g of catalyst, and a ratio of the medium strong acid content to the total acid content of 60 to 99%.

In a preferred embodiment, the catalyst has a medium strong acid content of 0.1 to 1 mmol/g, and a ratio of the medium strong acid content to the total acid content of 68-92%.

In the present application, Groups VB, VIB and VIIB metals are used as the first metal component of the aromatics conversion catalyst, so that the catalyst has the advantages of high reaction activity, low loss rate of aromatic hydrocarbon and the like. In a preferred embodiment, the first metal is selected from Mo, Re, W, or a combination thereof. In a further preferred embodiment, the first metal is at least two of Mo, Re and W, at a mixing ratio by weight of 0.1 to 10:1, calculated as metal element; or a combination of Mo, Re and W, at a weight ratio of Mo, Re and W of 1:0.1-0.4: 0.1-0.6.

According to the present application, the type of the second metal may be selected within a wide range, and any metal different from the first metal may be used, preferably the second metal is selected from the group consisting of Group IA metals, Group IIA metals, Group IIIA metals, Group IVA metals, Group VA metals, lanthanide series metals, and combinations thereof, more preferably selected from Sr, Bi, Ce, Zr, Ge, or combinations thereof.

In a preferred embodiment, the first metal component is immobilized on the acidic molecular sieve component by physical mixing and/or chemical bonding.

In a preferred embodiment, the second metal component is immobilized on the oxide additive, preferably by physical mixing and/or chemical bonding.

In a particularly preferred embodiment, the first metal component is immobilized on the acidic molecular sieve component by physical mixing and/or chemical bonding; and the second metal component is immobilized on the oxide additive by physical mixing and/or chemical bonding.

In the present application, it has been found for the first time that the distribution of the supported metal on the catalyst can be regulated and controlled in accordance with the influence of different metal components on the aromatics conversion process, wherein an effect of enhancing the aromatics conversion efficiency can be achieved by immobilizing Groups VB, VIB and VIIB metals with relatively stronger hydrogenation capability on the surface of the molecular sieve, and the hydrogenation saturation side reaction of aromatics on the surface of the oxide additive can be inhibited by immobilizing other metals on the oxide additive, so that the conversion efficiency and the selectivity of targeted products of the aromatics conversion catalyst when used in aromatics conversion reaction can be greatly improved.

According to the present application, the type of the acidic molecular sieve component may be selected within a wide range, and all commonly used acidic molecular sieve components may be used herein, which is preferably selected from acidic molecular sieves having eight-, ten- or twelve-membered ring pore structure; and is more preferably selected from the group consisting of ZSM-5 molecular sieves, MCM-22 molecular sieves, MOR molecular sieves, β molecular sieves, ZSM-12 molecular sieves, and combinations thereof.

According to the present application, the type of the oxide additive can be selected within a wide range, and all commonly used oxide additives can be used herein, which is preferably selected from alumina, magnesia, kaolin, or a combination thereof.

In the present application, the content of each component of the aromatics conversion catalyst can be selected within a wide range, and preferably, based on the total weight of the catalyst as 100 wt %, the acidic molecular sieve component is present in an amount of 40 to 90 wt %, the oxide additive is present in an amount of 5 to 40 wt %, the first metal component is present in an amount of 0.01 to 20 wt % (calculated as metal element), and the second metal component is present in an amount of 0.01 to 20 wt % (calculated as metal element).

In a preferred embodiment, based on the total weight of the aromatics conversion catalyst as 100 wt %, the acidic molecular sieve component is present in an amount of 50 to 80 wt %, the oxide additive is present in an amount of 10 to 30 wt %, the first metal component is present in an amount of 0.05 to 15 wt %, and the second metal component is present in an amount of 0.05 to 15 wt %.

Aromatics conversion catalysts meeting the aforementioned requirements of the present application may be used, of which the preparation method is not particularly limited. In a preferred embodiment, the aromatics conversion catalyst is prepared by the steps of: a) immobilizing a first metal component on the acidic molecular sieve; b) immobilizing a second metal component on the oxide additive; and c) shaping the product of step a) and the product of step b) by kneading.

In a more preferred embodiment, the aromatics conversion catalyst is prepared by a method comprising the steps of: a) impregnating an acidic molecular sieve component source with a first metal source solution, and carrying out a first heat treatment to obtain a first solid; b) impregnating an oxide additive source with a second metal source solution, and carrying out a second heat treatment to obtain a second solid; and c) shaping the first solid and the second solid by kneading. In the present application, the impregnation may be isovolumetric impregnation, supersaturated impregnation, or the like, preferably supersaturated impregnation.

In a preferred embodiment, the first heat treatment and the second heat treatment each comprises: roasting, or a combination of drying and roasting.

In a more preferred embodiment, each of the first and second heat treatments comprises a combination of drying and roasting.

In the present application, the drying conditions can be selected from a wide range, and common drying conditions can be used in the present application, and preferred drying conditions include: a temperature of 50-200° C., and a time of 1-30 h.

In the present application, the roasting conditions can be selected within a wide range, and all conventional roasting conditions can be used in the present application, and preferred roasting conditions include: conducting a heat treatment for 1 to 30 hours at a temperature of 300-700° C. under an oxygen-containing atmosphere.

In a preferred embodiment, the oxygen-containing atmosphere is a mixed gas of air and steam at a volume ratio of 5-100:1.

In the present application, the first metal source may be a soluble compound containing a Group VB, Group VIB, or Group VIIB metal. All commonly used soluble compounds can be used in the present application, such as nitrates, sulfates, chlorides (i.e., hydrochlorides), or ammonium salts, of which a detailed description is omitted herein for brevity.

In the present application, the second metal source may be a soluble compound containing the second metal. All commonly used soluble compounds can be used in the present application, such as nitrates, sulfates, chlorides or ammonium salts, of which a detailed description is omitted herein for brevity.

In the present application, the acidic molecular sieve component source can be, for example, an acidic molecular sieve selected from the group consisting of those having an eight-, ten- or twelve-membered ring pore structure, preferably selected from the group consisting of ZSM-5 molecular sieves, MCM-22 molecular sieves, MOR molecular sieves, β molecular sieves, ZSM-12 molecular sieves, and combinations thereof.

In the present application, the oxide additive source can be selected from, for example, alumina, magnesia, kaolin, precursors thereof, or combinations thereof.

According to the present application, the aromatics conversion catalyst can be used for disproportionation and transalkylation of alkyl aromatic hydrocarbons, and has the advantages of high reaction activity, low loss rate of aromatic hydrocarbon and the like.

The aromatics conversion catalyst of the present application may be reduced as necessary before use. The reduction step has no particular requirements, and may be carried out, for example, by introducing hydrogen for reduction or using other reducing agents, of which a detailed description is omitted herein for brevity.

In a preferred embodiment, the reaction conditions of step II) and step 2) include: a reaction temperature of 250-500° C., a reaction pressure of 1.5-6.5 MPa, a hydrogen-to-hydrocarbon molar ratio of 1-10, and a feeding weight hourly space velocity of 0.5-5 $h^{-1}$.

In a preferred embodiment, the purification of step III) and step 3) is aromatics extraction separation, non-aromatics selective cracking, or a combination thereof.

In some further preferred embodiments, the purification is an extraction separation carried out by extractive distillation using sulfolane solvent.

In the present application, the catalyst used in the non-aromatics selective cracking may be those conventionally used, for example, the catalyst may comprise 60 to 100 wt % of at least one acidic molecular sieve selected from the group consisting of those having an eight-, ten- or twelve-membered ring structure, such as at least one acidic molecular sieve selected from ZSM-5 molecular sieves, MCM-22 molecular sieves, MOR molecular sieves and β molecular sieves, and optionally 0.5 to 10 wt % of a metal component selected from Group VIB, VIIB and VIII metals.

In a preferred embodiment, the operating conditions for the non-aromatics selective cracking include: a reaction temperature of 300-600° C., a reaction pressure of 0.5-3.0 MPa, a hydrogen-to-hydrocarbon molar ratio of 1-10, and a feeding weight hourly space velocity of 1-15 $h^{-1}$.

In some preferred embodiments, the operating conditions for steam cracking in step IV) and step 4) include: a cracking temperature of 600-1000° C., a residence time of 0.01-0.8 s, and a reaction pressure of 0.1-0.3 MPa.

In some other preferred embodiments, the dehydrogenation reaction of step IV) and step 4) is carried out in the presence of a catalyst comprising from 0.05 to 20 wt % of a metal component selected from Pt, Pd, Cr, and Fe, and a balance amount of a carrier selected from alumina, silica, aluminosilicate, magnesia, and calcia; more preferably, the operating conditions of the dehydrogenation reaction include: a reaction temperature of 500-600° C., a weight hourly space velocity of 0.5-3.0 h$^{-1}$, and a reaction pressure of 0.3-1.5 MPa.

In a second aspect, the present application provides a system for carrying out the gasoline fraction processing method of the present application, comprising:

an aromatization unit for reacting the gasoline fraction therein and separating the resulting reaction product to obtain a $C_4^-$ component, a $C_5$ component, a $C_6$-$C_7$ component, a $C_8$ component and a $C_9^+$ component;

a cracking and aromatics conversion unit for reacting the $C_6$-$C_7$ component and the $C_9^+$ component from the aromatization unit and separating the resulting reaction product to obtain a $C_4^-$ component, a $C_5$ component, a $C_6$-$C_7$ component, a $C_8$ component and a $C_9^+$ component;

optionally, an aromatics purification unit for purifying at least one of the $C_8$ components from the aromatization unit and the cracking and aromatics conversion unit and separating the resultant to obtain a $C_4^-$ component, a $C_5$ component, a $C_6$-$C_7$ component, $C_8$ aromatic hydrocarbon(s) and a $C_9^+$ component;

optionally, a light hydrocarbon conversion unit for conducting steam cracking or dehydrogenation reaction on at least a part of at least one of the $C_4^-$ components from the aromatization unit, the cracking and aromatics conversion unit, and the optional aromatics purification unit; and optionally, a light gasoline blending unit for gasoline blending using at least a part of at least one of the $C_5$ components from the aromatization unit, the cracking and aromatics conversion unit, and the optional aromatics purification unit.

In some embodiments, the aromatization unit is provided with a gasoline fraction inlet, a $C_4^-$ component outlet, a $C_5$ component outlet, a $C_6$-$C_7$ component outlet, a $C_8$ component outlet, and a $C_9^+$ component outlet;

the cracking and aromatics conversion unit is provided with an inlet, a $C_4^-$ component outlet, a $C_5$ component outlet, a $C_6$-$C_7$ component outlet, a $C_8$ component outlet and a $C_9^+$ component outlet;

the aromatics purification unit is provided with an inlet, a $C_4^-$ component outlet, a $C_5$ component outlet, a $C_6$-$C_7$ component outlet, a $C_8$ aromatic hydrocarbon outlet and a $C_9^+$ component outlet;

the light hydrocarbon conversion unit is provided with an inlet and a conversion product outlet;

the light gasoline blending unit is provided with an inlet and a blended gasoline outlet, wherein the $C_6$-$C_7$ component outlet and the $C_9^+$ component outlet of the aromatization unit are communicated with the inlet of the cracking and aromatics conversion unit, optionally, at least one of the $C_8$ component outlet of the aromatization unit and the $C_8$ component outlet of the cracking and aromatics conversion unit is in communication with the inlet of the aromatics purification unit, at least one of the $C_4^-$ component outlet of the aromatization unit, the $C_4^-$ component outlet of the cracking and aromatics conversion unit, and the $C_4^-$ component outlet of the aromatics purification unit is in communication with the inlet of the light hydrocarbon conversion unit, Optionally, at least one of the $C_5$ component outlet of the aromatization unit, the $C_5$ component outlet of the cracking and aromatics conversion unit, and the $C_5$ component outlet of the aromatics purification unit is in communication with the inlet of the light gasoline blending unit, and the $C_6$-$C_7$ component outlet and the $C_9^+$ component outlet of the cracking and aromatics conversion unit, and optionally at least one of the $C_6$-$C_7$ component outlet and the $C_9^+$ component outlet of the aromatic purification unit, is in communication with the inlet of the cracking and aromatics conversion unit.

In a preferred embodiment, the aromatics purification unit may be an aromatics extraction separation unit, a non-aromatics selective cracking unit, or a combination thereof.

In preferred embodiments, the light hydrocarbon conversion unit may be a steam cracking unit, a dehydrogenation unit, or a combination thereof.

According to the present application, the aromatization unit may comprise an aromatization reactor and a separation device, wherein the aromatization reactor may be in the form of a fixed bed or moving bed commonly used in the art, such as an axial fixed bed reactor; the separation device may be in the form of a distillation, rectification or fractionation column commonly used in the art, for example an atmospheric or pressurized rectification column.

According to the present application, the cracking and aromatics conversion unit may comprise a cracking and aromatics conversion reactor and a separation device, wherein the cracking and aromatics conversion reactor may be in the form of a fixed bed commonly used in the art, such as a fixed bed reactor with intermediate quenching or a single-stage fixed bed reactor; the separation device may be in the form of a distillation, rectification or fractionation column commonly used in the art, such as an atmospheric rectification column.

According to the present application, the aromatics extraction separation unit may comprise an extraction separator and a separation device, wherein the extraction separator may be in the form of a liquid-liquid extractor, an extractive distillation column, or the like, commonly used in the art, such as an extractive distillation column using sulfolane solvent; the separation device may be in the form of a distillation, rectification or fractionation column commonly used in the art, for example an atmospheric or pressurized rectification column.

According to the present application, the non-aromatics selective cracking unit may comprise a cracking reactor and a separation device, wherein the cracking reactor may be in the form of a fixed bed reactor commonly used in the art, such as a radial fixed bed reactor, a fixed bed reactor with multistage of quenching; the separation device may be in the form of a distillation, rectification or fractionation column, commonly used in the art, for example an atmospheric or pressurized rectification column.

According to the present application, the steam cracking unit may be in the form of a gas cracking furnace commonly used in the art, such as an ultra short residence time cracking furnace, a short residence time cracking furnace.

According to the present application, the dehydrogenation unit may be in the form of a dehydrogenation reactor commonly used in the art, such as a fixed bed reactor.

According to the present application, in a preferred embodiment, the feed inlet and the discharge outlet of each unit are communicated with the feed inlet and the discharge outlet of relevant units through pipelines as needed, and further preferably, valves are independently arranged on each pipeline for regulating the flow rate.

When used for processing gasoline fractions, the system of the present application can effectively and directionally convert the gasoline fraction (such as catalytic gasoline fractions and LPG) into C8 aromatic hydrocarbon(s), and meanwhile produce light olefins and high-quality light gasoline as byproducts, so that an efficient comprehensive utilization can be achieved.

EXAMPLES

The present application will be further illustrated with reference to the following examples, but the present application is not limited thereto.

Preparation Examples of the Aromatics Conversion Catalyst of the Present Application All reagents used in the following preparation examples are commercially available, and have a purity of reagent pure grade.

In the following preparation examples, $NH_3$-TPD pattern of the resulting catalysts were measured by the following method: 100 mg of a sample crushed into 20-40 meshes was weighed, heated to 500° C. at a heating rate of 10° C./min under flowing nitrogen (30 ml/min), purged at a constant temperature for 30 minutes, cooled to 100° C. after the completion of the heat treatment, subjected to ammonia adsorption by introducing $NH_3$ gas and kept in the ammonia adsorption for 10 minutes, switched to helium purging (30 ml/min) for 1 hour, and heated to 600° C. by temperature programming at a heating rate of 10° C./min, and then a signal of the $NH_3$ concentration in the effluent was detected by TCD.

In the following preparation examples, the medium strong acid content of the catalyst was calculated according to the peak area within a temperature range of 200-400° C. of its $NH_3$-TPD pattern; the ratio of the medium strong acid content to the total acid content of the catalyst was the ratio of the peak area within a temperature range of 200-400° C. to the total peak area within a temperature range of 100-600° C. of its $NH_3$-TPD pattern.

In the following preparation examples, TEM images of the resulting catalysts were characterized by a high-resolution field emission transmission electron microscope, the operating voltage was 200 kV, and elemental analysis was performed by an energy scattering X-ray analyzer equipped on the transmission electron microscope.

Preparation Example 1

Figure 3:
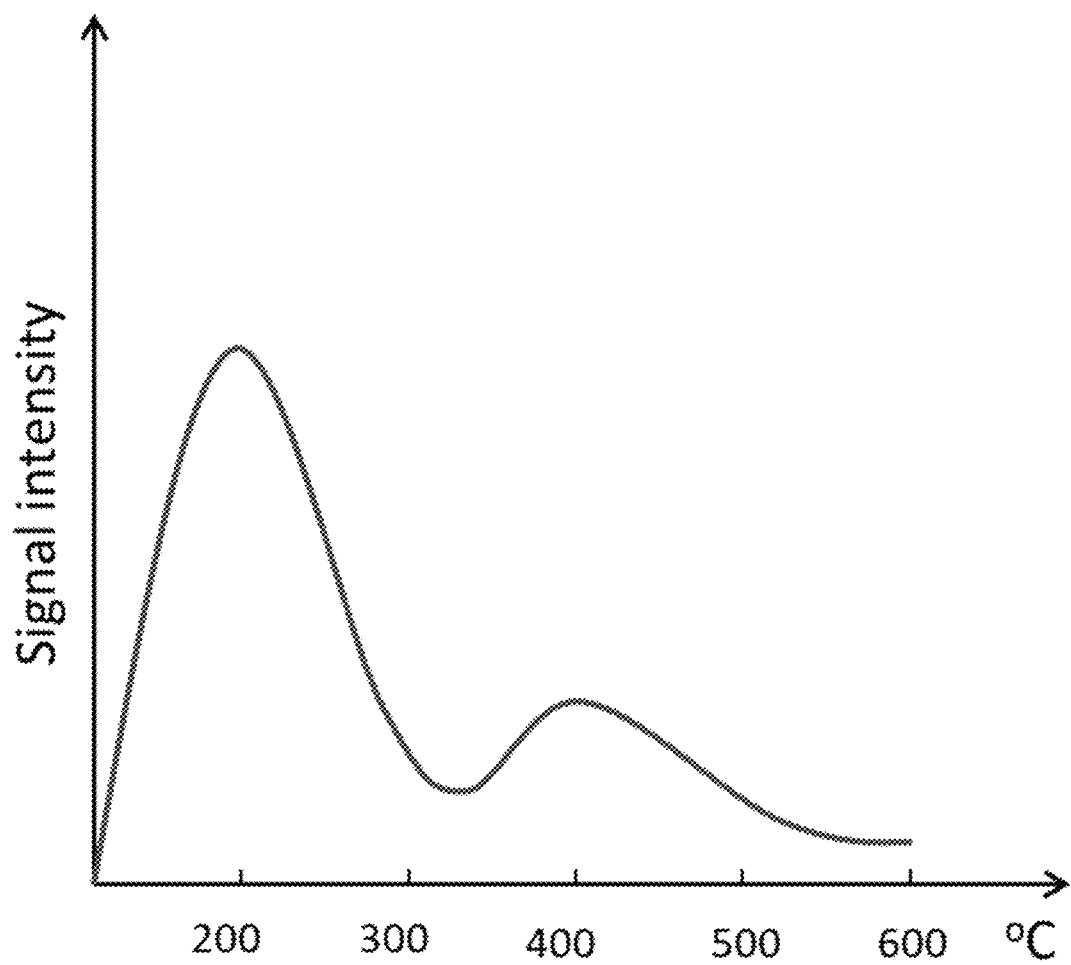
FIG. 3 shows the $NH_3$-TPD pattern of the catalyst obtained in Preparation Example 1 of the present application.

20 g of mordenite was taken, and subjected to supersaturated impregnation with an ammonium molybdate solution, the resultant was spray dried at 150° C., and then roasted for 3 hours at 400° C. under an air atmosphere to obtain a modified molecular sieve. 7.7 g of alumina was taken and isovolumetrically impregnated with strontium nitrate, and dried for 10 hours at 150° C. to obtain a modified alumina. The modified molecular sieve and the modified alumina were shaped by kneading, roasted at 550° C. for 2 hours to obtain a catalyst A with a molybdenum content of 1 wt % and a strontium content of 1.0 wt %. The composition and properties of the resulting catalyst are shown in Table 1, and the $NH_3$-TPD pattern of the resulting catalyst is shown in FIG. 3.

Figure 4:
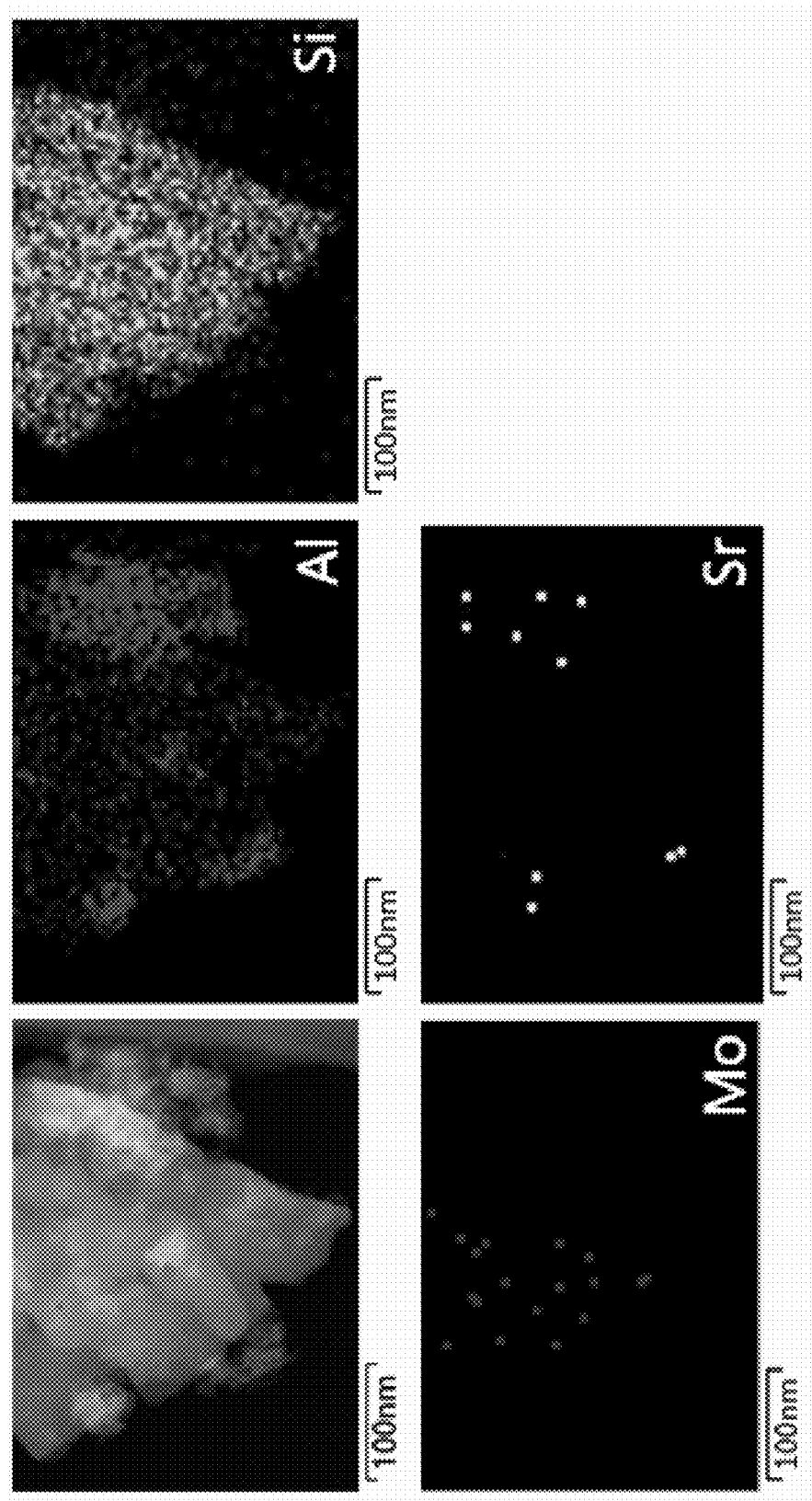
FIG. 4 shows a TEM image of the catalyst obtained in Preparation Example 1 of the present application.

The TEM elemental analysis of the resulting catalyst is shown in FIG. 4, in which the upper left image shows a TEM phase image of the combination of the molecular sieve and alumina, the upper middle image shows the distribution of the Al element, the upper right image shows the distribution of the Si element, the lower left image shows the distribution of the Mo element, and the lower middle image shows the distribution of the Sr element. From the composition of the resulting catalyst, it can be seen that the silicon-rich portion (see the upper right image) corresponds to the mordenite, while the aluminum-rich portion (see the upper middle image) corresponds to the alumina additive, and from the distribution of the Mo element (see the lower left image), it can be seen that the Mo element is mainly distributed on the surface of the mordenite in the catalyst, and the Sr element (see the lower middle image) is mainly distributed on the surface of the alumina additive.

Preparation Example 2

15 g of mordenite and 5 g of ZSM-5 molecular sieve were mixed, and subjected to supersaturated impregnation with an ammonium molybdate solution, and the resultant was dried for 10 hours at 120° C. and then roasted for 3 hours at 450° C. under an air atmosphere to obtain a modified molecular sieve. 7.7 g of alumina was taken and isovolumetrically impregnated with bismuth nitrate, dried for 10 hours at 120° C., and then roasted for 3 hours at 400° C. under an air atmosphere to obtain a modified alumina. The modified molecular sieve and the modified alumina were shaped by kneading, and roasted for 6 hours at 500° C. to obtain a catalyst B with a molybdenum content of 3 wt % and a bismuth content of 5 wt %, and the composition and properties of the resulting catalyst are shown in Table 1.

Preparation Example 3

15 g of mordenite and 5 g of ZSM-5 molecular sieve were taken, uniformly mixed, and subjected to supersaturated impregnation with an ammonium molybdate solution, the resultant was dried at 120° C. for 10 hours, and then roasted at 500° C. for 3 hours under an air atmosphere to obtain a modified molecular sieve. 7.7 g of alumina was taken and isovolumetrically impregnated with cerous nitrate, dried for 10 hours at 120° C., and then roasted for 3 hours at 400° C. under an air atmosphere to obtain a modified alumina. The modified molecular sieve and the modified alumina were shaped by kneading, and the resultant was roasted at 550° C. for 2 hours to obtain a catalyst C with a molybdenum content of 13 wt % and a cerium content of 8.0 wt %, and the composition and properties of the resulting catalyst are shown in Table 1.

Preparation Example 4

15 g of mordenite and 5 g of ZSM-5 molecular sieve were mixed, and subjected to supersaturated impregnation with an ammonium molybdate solution, and the resultant was subjected to fast spray drying at 160° C. and then roasted for 3 hours at 500° C. to obtain a modified molecular sieve. 7.7 g of alumina was taken and isovolumetrically impregnated with bismuth nitrate, dried for 10 hours at 160° C., and then roasted for 3 hours at 500° C. under an air atmosphere to obtain a modified alumina. The modified molecular sieve and the modified alumina were shaped by kneading, and roasted for 6 hours at 500° C. to obtain a catalyst D with a molybdenum content of 3 wt % and a bismuth content of 5 wt %, and the composition and properties of the resulting catalyst are shown in Table 1.

Preparation Example 5

15 g of mordenite and 5 g of ZSM-5 molecular sieve were mixed, and subjected to supersaturated impregnation with an ammonium molybdate solution, and the resultant was roasted for 3 hours at 500° C. to obtain a modified molecular sieve. 7.7 g of alumina was taken and isovolumetrically impregnated with bismuth nitrate, dried for 10 hours at 160° C., and then roasted for 3 hours at 500° C. under an air atmosphere to obtain a modified alumina. The modified molecular sieve and the modified alumina were shaped by kneading, and roasted at 550° C. for 3 hours to obtain a catalyst E with a molybdenum content of 3 wt % and a bismuth content of 5 wt %, and the composition and properties of the resulting catalyst are shown in Table 1.

Preparation Example 6

15 g of β molecular sieve and 5 g of ZSM-5 molecular sieve were uniformly mixed, and subjected to supersaturated impregnation with an ammonium perrhenate solution, the resultant was dried at 120° C. for 10 hours, and then roasted at 500° C. under an air atmosphere for 3 hours to obtain a modified molecular sieve. 7.7 g of alumina was taken and isovolumetrically impregnated with germanium chloride, dried for 10 hours at 120° C., and then roasted for 3 hours at 500° C. under an air atmosphere to obtain a modified alumina. The modified molecular sieve and the modified alumina were shaped by kneading, and roasted at 550° C. for 2 hours to obtain a catalyst F with a rhenium content of 1 wt % and a germanium content of 3.0 wt %, and the composition and properties of the resulting catalyst are shown in Table 1.

Preparation Example 7

15 g of ZSM-12 molecular sieve and 5 g of ZSM-5 molecular sieve were uniformly mixed, and subjected to isovolumetric impregnation with an ammonium molybdate solution, the resultant was dried at 120° C. for 10 hours, and then roasted at 400° C. under an air atmosphere for 3 hours to obtain a modified molecular sieve. 4 g of alumina and 3.5 g of magnesia were taken and uniformly mixed, then isovolumetrically impregnated with zirconium chloride, the resultant was dried for 10 hours at 120° C., and then roasted for 3 hours at 400° C. under an air atmosphere to obtain a modified oxide. The modified molecular sieve and the modified oxide were shaped by kneading, and the resultant was roasted at 500° C. for 4 hours to obtain a catalyst G with a molybdenum content of 8 wt % and a zirconium content of 5.0 wt %, and the composition and properties of the resulting catalyst are shown in Table 1.

Preparation Example 8

Catalyst I was prepared as described in Preparation Example 1, except that 18 g of mordenite and 2 g of ZSM-5 molecular sieve were uniformly mixed and subjected to isovolumetric impregnation with an ammonium molybdate and ammonium tungstate solution. The composition and properties of the resulting catalyst are shown in Table 1.

Preparation Example 9

Catalyst J was prepared as described in Preparation Example 1, except that 18 g of mordenite and 2 g of ZSM-5 molecular sieve were uniformly mixed and subjected to isovolumetric impregnation with an ammonium molybdate, ammonium tungstate and ammonium perrhenate solution. The composition and properties of the resulting catalyst are shown in Table 1.

Preparation Example 10

Catalyst M was prepared as described in Preparation Example 1, except that 18 g of mordenite and 2 g of ZSM-5 molecular sieve were uniformly mixed and subjected to isovolumetric impregnation with an ammonium molybdate solution, the resultant was dried at 120° C. for 10 hours, and then roasted at 400° C. for 3 hours under a mixed atmosphere of air and steam (at a volume ratio of air to steam of 20:1) to obtain a modified molecular sieve. The composition and properties of the resulting catalyst are shown in Table 1.

Preparation Example 11

Catalyst N was prepared as described in Preparation Example 1, except that 18 g of mordenite and 2 g of ZSM-5 molecular sieve were uniformly mixed and subjected to isovolumetric impregnation with an ammonium molybdate solution, the resultant was dried at 120° C. for 10 hours, and then roasted at 400° C. for 3 hours under a mixed atmosphere of air and steam (at a volume ratio of air to steam of 5:1) to obtain a modified molecular sieve. The composition and properties of the resulting catalyst are shown in Table 1.

Preparation Example 12

Catalyst O was prepared as described in Preparation Example 1, except that 18 g of mordenite and 2 g of ZSM-5 molecular sieve were uniformly mixed and subjected to isovolumetric impregnation with an ammonium molybdate solution, and the resultant was dried at 120° C. to obtain a modified molecular sieve; 7.7 g of alumina was isovolumetrically impregnated with strontium nitrate, and dried at 150° C. to obtain a modified alumina; the modified molecular sieve and the modified alumina were shaped by kneading, and roasted at 550° C. for 2 hours to obtain a catalyst. The composition and properties of the resulting catalyst are shown in Table 1.

Preparation Example 13

Catalyst P was prepared as described in Preparation Example 1, except that 20 g of mordenite was taken and subjected to isovolumetric impregnation with an ammonium molybdate and ammonium tungstate solution. The composition and properties of the resulting catalyst are shown in Table 1.

Preparation Example 14

Catalyst Q was prepared as described in Preparation Example 1, except that 20 g of ZSM-5 molecular sieve was taken and subjected to isovolumetric impregnation with an ammonium molybdate and ammonium tungstate solution. The composition and properties of the resulting catalyst are shown in Table 1.

Preparation Example 15

Catalyst R was prepared as described in in Preparation Example 1, except that 20 g of β molecular sieve was taken and subjected to isovolumetric impregnation with an ammonium molybdate and ammonium tungstate solution. The composition and properties of the resulting catalyst are shown in Table 1.

Preparation Example 16

Catalyst S was prepared as described in Preparation Example 1, except that 20 g of MCM-22 molecular sieve was taken and subjected to isovolumetric impregnation with an ammonium molybdate and ammonium tungstate solution. The composition and properties of the resulting catalyst are shown in Table 1.

Preparation Example 17

Catalyst T was prepared as described in Preparation Example 1, except that 18 g of MCM-22 molecular sieve and 2 g of ZSM-5 molecular sieve were taken and subjected to isovolumetric impregnation with an ammonium molybdate and ammonium tungstate solution. The composition and properties of the resulting catalyst are shown in Table 1.

Preparation Example 18

Catalyst U was prepared as described in Preparation Example 1, except that an equivalent amount of kaolin was used instead of alumina as the oxide adjuvant. The composition and properties of the resulting catalyst are shown in Table 1.

TABLE 1

Composition of the catalyst obtained in each preparation example

| Preparation example No. | Catalyst No. | Content of first metal component, calculated as metal element, wt % | Content of second metal component, calculated as metal element, wt % | Type of molecular sieve | Content of molecular sieve component, wt % | Type of oxide additive | Content of oxide additive, wt % | Mediate strong acid content, mmol/g · cat | Ratio of mediate strong acid content to total acid content, % |
|---|---|---|---|---|---|---|---|---|---|
| 1 | A | Mo, 1% | Sr, 1.0% | Mordenite | 71 | Alumina | 27 | 0.59 | 72 |
| 2 | B | Mo, 3% | Bi, 5% | Mordenite + ZSM-5 molecular sieve | 67 | Alumina | 25 | 0.54 | 83 |
| 3 | C | Mo, 13% | Ce, 8.0% | Mordenite + ZSM-5 molecular sieve | 60 | Alumina | 19 | 0.12 | 90 |
| 4 | D | Mo, 3% | Bi, 5% | Mordenite + ZSM-5 molecular sieve | 67 | Alumina | 25 | 0.54 | 83 |
| 5 | E | Mo, 3% | Bi, 5% | Mordenite + ZSM-5 molecular sieve | 67 | Alumina | 25 | 0.51 | 85 |
| 6 | F | Re, 1% | Ge, 3.0% | β molecular sieve + ZSM-5 molecular sieve | 69 | Alumina | 27 | 0.45 | 68 |
| 7 | G | Mo, 8% | Zr, 5.0% | ZSM-12 + ZSM-5 molecular sieve | 64 | Alumina + magnesia | 23 | 0.31 | 87 |
| 8 | I | Mo, 2% W, 1% | Sr, 1.0% | Mordenite + ZSM-5 molecular sieve | 69 | Alumina | 27 | 0.58 | 82 |
| 9 | J | Mo, 2% W, 0.5% Re, 0.5% | Sr, 1.0% | Mordenite + ZSM-5 molecular sieve | 69 | Alumina | 27 | 0.57 | 85 |
| 10 | M | Mo, 2% | Sr, 1.0% | Mordenite + ZSM-5 molecular sieve | 70 | Alumina | 27 | 0.50 | 88 |
| 11 | N | Mo, 2% | Sr, 1.0% | Mordenite + ZSM-5 molecular sieve | 70 | Alumina | 27 | 0.52 | 90 |
| 12 | O | Mo, 2% | Sr, 1.0% | Mordenite + ZSM-5 molecular sieve | 70 | Alumina | 27 | 0.61 | 75 |
| 13 | P | Mo, 2% W, 1% | Sr, 1.0% | Mordenite | 70 | Alumina | 27 | 0.55 | 80 |
| 14 | Q | Mo, 2% W, 1% | Sr, 1.0% | ZSM-5 molecular sieve | 70 | Alumina | 27 | 0.51 | 76 |

TABLE 1-continued

Composition of the catalyst obtained in each preparation example

| Preparation example No. | Catalyst No. | Content of first metal component, calculated as metal element, wt % | Content of second metal component, calculated as metal element, wt % | Type of molecular sieve | Content of molecular sieve component, wt % | Type of oxide additive | Content of oxide additive, wt % | Mediate strong acid content, mmol/g · cat | Ratio of mediate strong acid content to total acid content, % |
|---|---|---|---|---|---|---|---|---|---|
| 15 | R | Mo, 2% W, 1% | Sr, 1.0% | β molecular sieve | 70 | Alumina | 27 | 0.43 | 83 |
| 16 | S | Mo, 2% W, 1% | Sr, 1.0% | MCM-22 molecular sieve | 70 | Alumina | 27 | 0.30 | 85 |
| 17 | T | Mo, 2% W, 1% | Sr, 1.0% | MCM-22 + ZSM-5 molecular sieve | 70 | Alumina | 27 | 0.34 | 82 |
| 18 | U | Mo, 2% | Sr, 1.0% | Mordenite + ZSM-5 molecular sieve | 70 | Kaolin | 27 | 0.51 | 88 |

Examples of Method for Processing Gasoline Fractions

Examples 1-2 below illustrate the practice of the processing method of the present application using conventional catalysts, wherein each catalyst used was prepared by conventional methods known in the art, unless otherwise specified.

Example 1

Referring to the flow chart shown in FIG. 1, a catalytic cracking gasoline (100 tons/hour) was subjected to desulfurization and denitrification, and then passed through an aromatization unit for aromatization reaction, and the resulting product was split into a $C_4^-$ component, a $C_5$ component, a $C_6$-$C_7$ component, a $C_8$ component and a $C_9^+$ component according to the boiling range. The $C_4^-$ component in the product was used as a cracking raw material to carry out steam cracking; the $C_5$ component had a low olefin content and a high isoparaffin content, and was used as a high-quality light gasoline blending component; the $C_8$ component was sent to a non-aromatics cracking unit to produce high-purity $C_8$ aromatic hydrocarbon(s); the $C_6$-$C_7$ and $C_9^+$ components were sent to a cracking and aromatics conversion unit to increase the yield of light hydrocarbon and $C_8$ aromatic hydrocarbon. From the cracking and aromatics conversion unit, the $C_4^-$ component obtained as a by-product was used as a steam cracking raw material, the $C_5$ component was used as a high-quality light gasoline blending component for gasoline blending, the $C_8$ component was sent to the non-aromatics cracking unit to produce high-purity $C_8$ aromatic hydrocarbon(s), and unreacted $C_6$-$C_7$ and $C_9^+$ components were recycled to the cracking and aromatics conversion unit. In the non-aromatics cracking unit, non-aromatic hydrocarbons in the $C_8$ component were further cracked to produce high-purity $C_8$ aromatic hydrocarbon(s) and cracked light hydrocarbons, wherein the $C_8$ aromatic hydrocarbon(s) was recovered as a product, the $C_4^-$ components was used as a steam cracking raw material, the $C_5$ component was used as a high-quality light gasoline blending component, and the $C_6^+$ heavy fraction was partially or completely recycled to the cracking and aromatics conversion unit.

In the aromatization unit, the catalyst used was a Zn-modified ZSM-5 molecular sieve, with a Zn content (calculated as metal element) of 2 wt %, a ZSM-5 molecular sieve content of 70 wt %, and the rest being alumina, the reaction temperature was 500° C., the reaction pressure was 0.5 MPa, and the feeding weight hourly space velocity was 1.5 h$^{-1}$; in the cracking and aromatics conversion unit, the catalyst used was a Pt-modified mordenite, with a Pt content (calculated as metal element) of 0.05 wt %, a mordenite content of 70 wt %, and the rest being alumina, the reaction temperature was 350° C., the reaction pressure was 3.0 MPa, the feeding weight hourly space velocity was 3.0 h$^{-1}$, and the hydrogen-to-hydrocarbon molar ratio was 3.0; and in the non-aromatics cracking unit, the catalyst used was a ZSM-5 molecular sieve catalyst, the reaction temperature was 450° C., the reaction pressure was 3.0 MPa, the feeding weight hourly space velocity was 1.0 h$^{-1}$, and the hydrogen-to-hydrocarbon molar ratio was 4.0.

The properties of the catalytic cracking gasoline raw material, the reaction conditions of each unit, and the product yield of the integrated unit are shown in Table 2, Table 3 and Table 4, respectively.

Example 2

Figure 2:
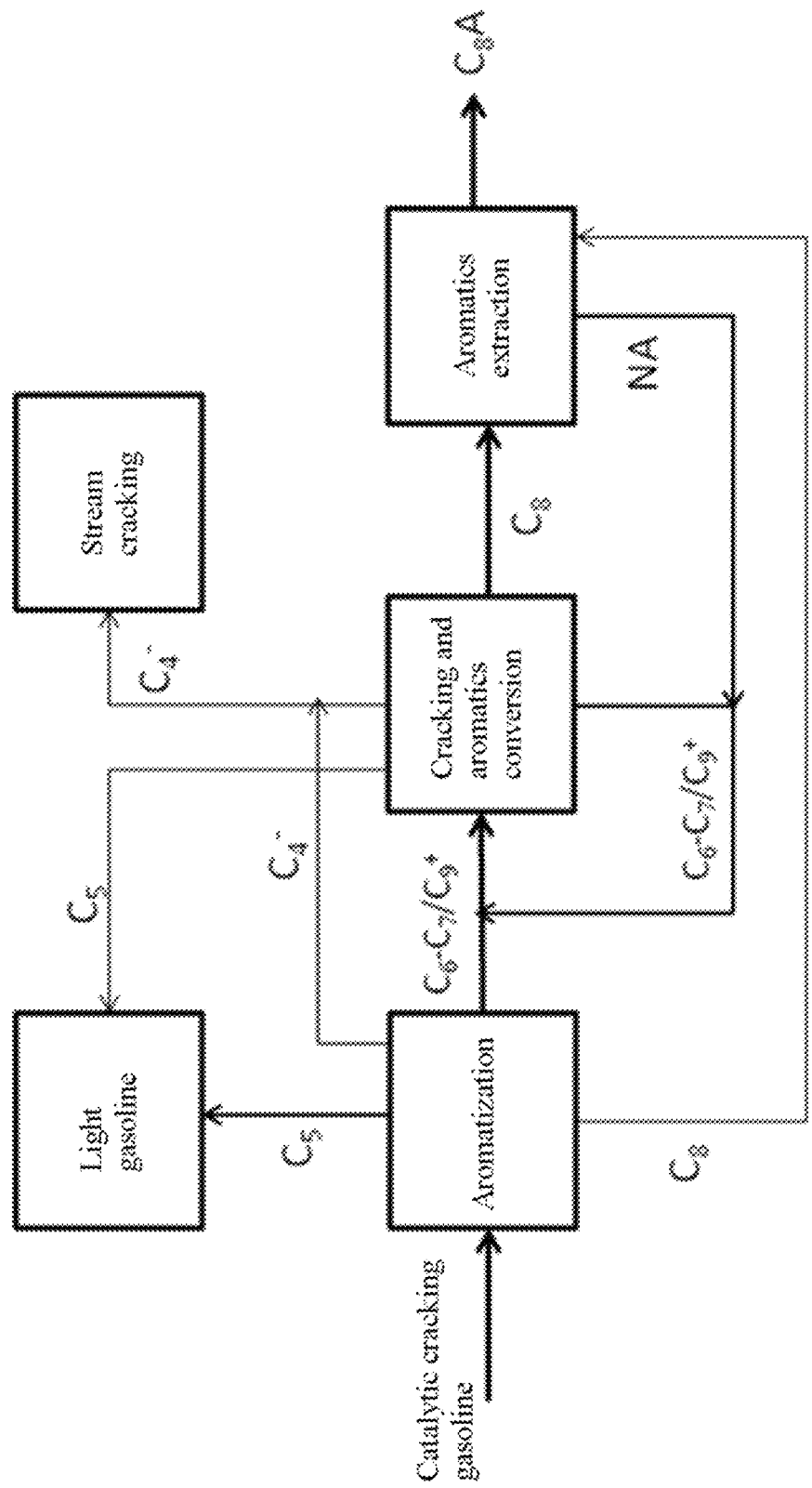
FIG. 2 is a schematic flow diagram of another preferred embodiment of the method according to the present application.

Referring to the flow chart shown in FIG. 2, a catalytic cracking gasoline (100 tons/hour) was subjected to desulfurization and denitrification, and then passed through an aromatization unit for aromatization reaction, and the resulting product was split into a $C_4^-$ component, a $C_5$ component, a $C_6$-$C_7$ component, a $C_8$ component and a $C_9^+$ component according to the boiling range. The $C_4^-$ component in the product was used as a cracking raw material to carry out steam cracking; the $C_5$ component had a low olefin content and a high isoparaffin content, and was used as a high-quality light gasoline blending component for light gasoline blending; the $C_8$ component was sent to an aromatics extraction unit to produce high-purity $C_8$ aromatic hydrocarbon(s); the $C_6$-$C_7$ and $C_9^+$ components were sent to a cracking and aromatics conversion unit to increase the yield of light hydrocarbon and $C_8$ aromatic hydrocarbon. From the cracking and aromatics conversion unit, the $C_4^-$ component obtained as a by-product was used as a steam cracking raw material, the $C_5$ component was used as a high-quality light gasoline blending component, the $C_8$ component was sent to the aromatics extraction unit to produce high-purity $C_8$ aromatic hydrocarbon(s), and unreacted $C_6$-$C_7$ and $C_9^+$ components were recycled to the cracking and aromatics conversion unit. In the aromatics extraction unit, the aromatic and non-aromatic hydrocarbons in the $C_8$ component were separated, wherein the $C_8$ aromatic hydrocarbons were recovered as a product, and the non-aromatic hydrocarbons was partially or completely recycled to the cracking and aromatics conversion unit.

In the aromatization unit, the catalyst used was a Zn-modified ZSM-5 molecular sieve, with a Zn content (calculated as metal element) of 3 wt %, a ZSM-5 molecular sieve content of 70 wt %, and the rest being alumina, the reaction temperature was 450° C., the reaction pressure was 1.0 MPa, and the feeding weight hourly space velocity was 1.0 $h^{-1}$; in the cracking and aromatics conversion unit, the catalyst used was a Mo-modified zeolite, with a Mo content (calculated as metal element) of 4 wt %, a β zeolite content of 70 wt %, and the rest being alumina, the reaction temperature was 380° C., the reaction pressure was 3.0 MPa, the feeding weight hourly space velocity was 3.0 $h^{-1}$, and the hydrogen-to-hydrocarbon molar ratio was 3.0.

The properties of the catalytic cracking gasoline raw material, the reaction conditions of each unit, and the product yield of the integrated unit are shown in Table 2, Table 3, and Table 4, respectively.

TABLE 2

Properties of the raw materials used in the examples

| Raw materials | Example 1 Catalytic cracking gasoline | Example 2 Catalytic cracking gasoline |
|---|---|---|
| Sulfur content, ppm-wt | 4 | 2 |
| Nitrogen content, ppm-wt | 2 | 0.5 |
| Aromatics, wt % | 35 | 20 |
| Olefins, wt % | 25 | 36 |
| Paraffins, wt % | 40 | 44 |
| Distillation range, ° C. | 70-200 | 50-180 |

TABLE 3

Reaction conditions of Examples 1-2

| | Example 1 | Example 2 |
|---|---|---|
| Reaction unit Aromatization unit | | |
| Temperature, ° C. | 500 | 450 |
| Pressure, MPa | 0.5 | 1.0 |
| Weight hourly space velocity, $h^{-1}$ | 1.5 | 1.0 |
| Cracking and aromatics conversion unit | | |
| Temperature, ° C. | 350 | 380 |
| Pressure, MPa | 3.0 | 3.0 |
| Weight hourly space velocity, $h^{-1}$ | 3.0 | 3.0 |
| Hydrogen-to-hydrocarbon molar ratio | 3.0 | 3.0 |

TABLE 3-continued

Reaction conditions of Examples 1-2

| | Example 1 | Example 2 |
|---|---|---|
| Non-aromatics cracking unit | | |
| Temperature, ° C. | 450 | |
| Pressure, MPa | 3.0 | |
| Weight hourly space velocity, $h^{-1}$ | 1.0 | |
| Hydrogen-to-hydrocarbon molar ratio | 4.0 | |
| Steam cracking unit | | |
| Temperature, ° C. | 850 | 850 |

TABLE 4

Test results of Examples 1-2

| Products | Example 1 Yield, t/h | Example 2 Yield, t/h |
|---|---|---|
| Ethylene | 18 | 25 |
| Propylene | 15 | 13 |
| $C_8$ aromatic hydrocarbons | 45 | 40 |
| Light gasoline | 7 | 8 |
| $C_{10}^+$ | 2 | 1 |
| Others | 13 | 13 |

As can be seen from the test results in Table 4, the method of the present application can be applied to the processing of gasoline fractions having different composition, and the yield of olefins and $C_8$ aromatic hydrocarbons in the product can reach 70-80%.

The following Examples 3-20 illustrate the practice of the processing method of the present application using the aromatics conversion catalyst of the present application.

Examples 3 to 20

Before use, Catalysts A to U obtained in Preparation Examples 1 to 18 were separately placed in a reactor, and reduced with an introduction of hydrogen gas at 450° C. for 3 hours. Then, a gasoline raw material was processed in the same manner as in Example 1, except that the aromatics conversion catalysts used in Example 1 was replaced with Catalysts A to U, respectively, with other operating conditions being the same, and the results are shown in Table 5.

Example 21

A gasoline raw material was processed as described in Example 10, except that the steam cracking unit used in Example 10 was replaced with a dehydrogenation unit, and the dehydrogenation catalyst used was $Cr_2O_3$ modified alumina, with a Cr content (calculated as metal element) of 8 wt %, and the rest being alumina, the dehydrogenation temperature was 560° C., the reaction pressure was 0.8 MPa, the feeding weight hourly space velocity was 2 $h^{-1}$, with other operating conditions being the same, and the results are shown in Table 5.

TABLE 5

Test results of Examples 3-21

| Products | Example 3 Yield, t/h | Example 4 Yield, t/h | Example 5 Yield, t/h |
|---|---|---|---|
| Ethylene | 20 | 22 | 23 |
| Propylene | 15 | 16 | 17 |
| $C_8$ aromatic hydrocarbons | 48 | 48 | 46 |
| Light gasoline | 5 | 4 | 3 |
| $C_{10}^+$ | 2.0 | 1.5 | 1 |
| Others | 10 | 8.5 | 10 |

| Products | Example 6 Yield, t/h | Example 7 Yield, t/h | Example 8 Yield, t/h |
|---|---|---|---|
| Ethylene | 23 | 21 | 22 |
| Propylene | 16 | 17 | 16 |
| $C_8$ aromatic hydrocarbons | 47 | 48 | 48 |
| Light gasoline | 4 | 4 | 5 |
| $C_{10}^+$ | 1.4 | 1.6 | 1 |
| Others | 8.6 | 8.4 | 8 |

| Products | Example 9 Yield, t/h | Example 10 Yield, t/h | Example 11 Yield, t/h |
|---|---|---|---|
| Ethylene | 24 | 22 | 23 |
| Propylene | 16 | 15 | 15 |
| $C_8$ aromatic hydrocarbons | 46 | 51 | 50 |
| Light gasoline | 3 | 4 | 4 |
| $C_{10}^+$ | 1.3 | 1.2 | 1.1 |
| Others | 9.7 | 6.8 | 6.9 |

| Products | Example 12 Yield, t/h | Example 13 Yield, t/h | Example 14 Yield, t/h |
|---|---|---|---|
| Ethylene | 22 | 21 | 21 |
| Propylene | 16 | 15 | 15 |
| $C_8$ aromatic hydrocarbons | 51 | 52 | 48 |
| Light gasoline | 3 | 4 | 5 |
| $C_{10}^+$ | 1 | 0.8 | 1.8 |
| Others | 7 | 7.2 | 9.2 |

| Products | Example 15 Yield, t/h | Example 16 Yield, t/h | Example 17 Yield, t/h |
|---|---|---|---|
| Ethylene | 20 | 25 | 18 |
| Propylene | 13 | 18 | 12 |
| $C_8$ aromatic hydrocarbons | 51 | 42 | 52 |
| Light gasoline | 4 | 3 | 6 |
| $C_{10}^+$ | 2 | 0.4 | 3 |
| Others | 10 | 11.6 | 9 |

| Products | Example 18 Yield, t/h | Example 19 Yield, t/h | Example 20 Yield, t/h |
|---|---|---|---|
| Ethylene | 17 | 21 | 22 |
| Propylene | 13 | 14 | 15 |
| $C_8$ aromatic hydrocarbons | 53 | 50 | 48 |
| Light gasoline | 6 | 5 | 6 |
| $C_{10}^+$ | 2 | 1.6 | 1.3 |
| Others | 9 | 8.4 | 7.7 |

| Products | Example 21 Yield, t/h |
|---|---|
| Ethylene | 23 |
| Propylene | 13 |
| $C_8$ aromatic hydrocarbons | 51 |
| Light gasoline | 4 |
| $C_{10}^+$ | 1.2 |
| Others | 7.8 |

As can be seen from the test results in Table 5, the total yield of olefins and $C_8$ aromatic hydrocarbons can be further increased by using the aromatics conversion catalyst of the present application, and in a preferred embodiment, the total yield of ($C_8$ aromatics+ethylene+propylene) can reach 89 wt % or higher.

The present application is illustrated in detail hereinabove with reference to preferred embodiments, but is not intended to be limited to those embodiments. Various modifications may be made following the inventive concept of the present application, and these modifications shall be within the scope of the present application.

It should be noted that the various technical features described in the above embodiments may be combined in any suitable manner without contradiction, and in order to avoid unnecessary repetition, various possible combinations are not described in the present application, but such combinations shall also be within the scope of the present application.

In addition, the various embodiments of the present application can be arbitrarily combined as long as the combination does not depart from the spirit of the present application, and such combined embodiments should be considered as the disclosure of the present application.

The invention claimed is:

1. A method for processing a gasoline fraction, comprising the steps of:
   I) reacting the gasoline fraction in an aromatization unit and separating the resulting reaction product to obtain a $C_4^-$ component, a $C_5$ component, a $C_6$-$C_7$ component, a $C_8$ component and a $C_9^+$ component, wherein the reaction occurring in the aromatization unit includes aromatization reaction;
   II) reacting the $C_6$-$C_7$ component and the $C_9^+$ component from step I) in a cracking and aromatics conversion unit, and separating the resulting reaction product to obtain a $C_4^-$ component, a $C_5$ component, a $C_6$-$C_7$ component, a $C_8$ component and a $C_9^+$ component, wherein the reaction occurring in the cracking and aromatics conversion unit includes non-aromatics cracking reaction and transalkylation reaction;
   III) purifying at least one of the $C_8$ components from steps I) and II), and separating the resultant to obtain a $C_4^-$ component, a $C_5$ component, a $C_6$-$C_7$ component, $C_8$ aromatic hydrocarbon(s) and a $C_9^+$ component;
   IV) subjecting at least a part of at least one of the $C_4^-$ components from steps I), II), and III) to steam cracking or dehydrogenation reaction;
   V) using at least a part of at least one of the $C_5$ components from steps I), II), and III) for gasoline blending; and
   VI) recycling the $C_6$-$C_7$ component and the $C_9^+$ component from step II), and optionally at least a part of at least one of the $C_6$-$C_7$ component and the $C_9^+$ component from step III), to the cracking and aromatics conversion unit of step II) for further reaction.

2. A method for processing a gasoline fraction, comprising the steps of:

1) reacting the gasoline fraction in the presence of an aromatization catalyst, and separating the resulting reaction product to obtain a $C_4^-$ component, a $C_5$ component, a $C_6$-$C_7$ component, a $C_8$ component and a $C_9^+$ component, wherein the reaction includes aromatization reaction;

2) reacting the $C_6$-$C_7$ component and the $C_9^+$ component from step 1) in the presence of an aromatics conversion catalyst, and separating the resulting reaction product to obtain a $C_4^-$ component, a $C_5$ component, a $C_6$-$C_7$ component, a $C_8$ component and a $C_9^+$ component, wherein the reaction includes non-aromatics cracking reaction and transalkylation reaction;

3) purifying at least one of the $C_8$ components from steps 1) and 2), and separating the resultant to obtain a $C_4^-$ component, a $C_5$ component, a $C_6$-$C_7$ component, $C_8$ aromatic hydrocarbon(s) and a $C_9^+$ component;

4) subjecting at least a part of at least one of the $C_4^-$ components from steps 1), 2), and 3) to steam cracking or dehydrogenation reaction;

5) using at least a part of at least one of the $C_5$ components from steps 1), 2), and 3) for gasoline blending; and 6) recycling the $C_6$-$C_7$ component and the $C_9^+$ component from step 2), and optionally at least a part of at least one of the $C_6$-$C_7$ component and the $C_9^+$ component from step 3), to step 2) for further reaction in the presence of the aromatics conversion catalyst.

3. The method of claim 1, wherein the gasoline fraction used in step I) has one or more of the following characteristics:
a boiling range of 40-250° C.;
an aromatics content of 10 to 100 wt %; and
being selected from the group consisting of catalytic cracking gasoline, hydrocracking gasoline, ethylene cracking gasoline, catalytic reformate, straight-run gasoline, LPG, mixtures thereof, and a partial fraction thereof.

4. The method of claim 1, wherein the aromatization catalyst used in the aromatization unit of step I) comprises, based on the weight of the catalyst, 50 to 90 wt % of a molecular sieve selected from aluminosilicates, aluminogallosilicates, aluminosilicophosphates, aluminoferrosilicates having a ten- or twelve-membered ring pore structure, and a combination thereof, and 0.5 to 10 wt % of a modifying metal selected from the group consisting of Group IB, Group IIB, Group VIB, Group VIIB, and Group VIII metals,
and/or, the reaction conditions of step I) include: a reaction temperature of 400-600° C., a reaction pressure of 0.2-3 MPa, and a feeding weight hourly space velocity of 0.5-5 $h^{-1}$.

5. The method of claim 1, wherein the aromatics conversion catalyst used in the cracking and aromatics conversion unit of step II) comprises an acidic molecular sieve component, an oxide additive, a first metal component immobilized on the acidic molecular sieve component, and a second metal component, wherein the first metal of the first metal component is selected from the group consisting of Group VB metals, Group VIB metals, Group VIIB metals, and combinations thereof, wherein the second metal of the second metal component is a metal different from the first metal, the catalyst has a medium strong acid content of 0.05-2.0 mmol/g of catalyst, and a ratio of medium strong acid content to total acid content of 60-99%,
and/or, the reaction conditions of step II) include: a reaction temperature of 250-500° C., a reaction pressure of 1.5-6.5 MPa, a hydrogen-to-hydrocarbon molar ratio of 1-10, and a feeding weight hourly space velocity of 0.5-5 $h^{-1}$.

6. The method of claim 5, wherein the first metal component is immobilized on the acidic molecular sieve component by physical mixing and/or chemical bonding; and the second metal component is immobilized on the oxide additive by physical mixing and/or chemical bonding.

7. The method of claim 5, wherein the aromatics conversion catalyst has an acidic molecular sieve component content of 40 to 90 wt %, an oxide additive content of 5 to 40 wt %, a first metal component content of 0.01 to 20 wt %, and a second metal component content of 0.01 to 20 wt %, based on the total weight of the catalyst.

8. The method of claim 5, wherein the aromatics conversion catalyst has one or more of the following characteristics:
the acidic molecular sieve component is selected from acidic molecular sieve components having an eight-, ten- or twelve-membered ring pore structure, ZSM-5 molecular sieves, MCM-22 molecular sieves, MOR molecular sieves, β molecular sieves, ZSM-12 molecular sieves, and combinations thereof;
the first metal is selected from the group consisting of Mo, Re, and W thereof, or
the first metal is a combination of two of Mo, Re, and W at a mixing ratio by weight of 0.1-10:1, calculated as metal element, or
the first metal is a combination of Mo, Re, and W at a weight ratio of Mo, Re and W of 1:0.1-0.4:0.1-0.6, calculated as metal element;
the second metal is selected from the group consisting of Group IA metals, Group IIA metals, Group IIIA metals, Group IVA metals, Group VA metals, lanthanide series metals, Sr, Bi, Ce, Zr, Ge, and combinations thereof; and
the oxide additive is selected from the group consisting of alumina, magnesia, kaolin, and a combination thereof.

9. The method of claim 1, wherein:
the purifying of step III) comprises subjecting the $C_8$ component to aromatics extraction separation, non-aromatics selective cracking, or a combination thereof, or
the purifying comprises subjecting the $C_8$ component to extraction separation by extractive distillation using sulfolane solvent; or
the purifying comprises subjecting the $C_8$ component to non-aromatics selective cracking in the presence of a catalyst comprising a molecular sieve component selected from the group consisting of ZSM-5 molecular sieves, MCM-22 molecular sieves, MOR molecular sieves, β molecular sieves, and combinations thereof, and optionally a metal component selected from Group VIB metals, Group VIIB metals, and Group VIII metals;
and/or, the operating conditions for the non-aromatics selective cracking include: a reaction temperature of 300-600° C., a reaction pressure of 0.5-3.0 MPa, a hydrogen-to-hydrocarbon molar ratio of 1-10, and a feeding weight hourly space velocity of 1-15 $h^{-1}$.

10. The method of claim 1, wherein the operating conditions of the steam cracking of step IV) include: a cracking temperature of 600-1000° C., a residence time of 0.01-0.8 s, and a reaction pressure of 0.1-0.3 MPa; or
the operating conditions of the dehydrogenation reaction in step IV) include: a reaction temperature of 400-700°

C., a weight hourly space velocity of 0.5-10, and a reaction pressure of 0.1-2 MPa.

11. A system for carrying out the gasoline fraction processing method of claim 1, comprising:
an aromatization unit for reacting the gasoline fraction therein and separating the resulting reaction product to obtain a $C_4^-$ component, a $C_5$ component, a $C_6$-$C_7$ component, a $C_8$ component and a $C_9^+$ component;
a cracking and aromatics conversion unit for reacting the $C_6$-$C_7$ component and the $C_9^+$ component from the aromatization unit and separating the resulting reaction product to obtain a $C_4^-$ component, a $C_5$ component, a $C_6$-$C_7$ component, a $C_8$ component and a $C_9^+$ component;
an aromatics purification unit for purifying at least one of the $C_8$ components from the aromatization unit and the cracking and aromatics conversion unit and separating the resultant to obtain a $C_4^-$ component, a $C_5$ component, a $C_6$-$C_7$ component, $C_8$ aromatic hydrocarbon(s) and a $C_9^+$ component;
a light hydrocarbon conversion unit for conducting steam cracking or dehydrogenation reaction on at least a part of at least one of the $C_4^-$ components from the aromatization unit, the cracking and aromatics conversion unit, and the optional aromatics purification unit; and
a light gasoline blending unit for gasoline blending using at least a part of at least one of the $C_5$ components from the aromatization unit, the cracking and aromatics conversion unit, and the optional aromatics purification unit,
wherein:
the aromatization unit is provided with a gasoline fraction inlet, a $C_4^-$ component outlet, a $C_5$ component outlet, a $C_6$-$C_7$ component outlet, a $C_8$ component outlet and a $C_9^+$ component outlet;
the cracking and aromatics conversion unit is provided with an inlet, a $C_4^-$ component outlet, a $C_5$ component outlet, a $C_6$-$C_7$ component outlet, a $C_8$ component outlet and a $C_9^+$ component outlet;
the aromatics purification unit is provided with an inlet, a $C_4^-$ component outlet, a $C_5$ component outlet, a $C_6$-$C_7$ component outlet, a $C_8$ aromatic hydrocarbon outlet and a $C_9^+$ component outlet:
the light hydrocarbon conversion unit is provided with an inlet and a conversion product outlet;
the light gasoline blending unit is provided with an inlet and a blended gasoline outlet,
wherein the $C_6$-$C_7$ component outlet and the $C_9^+$ component outlet of the aromatization unit are in communication with the inlet of the cracking and aromatics conversion unit,
at least one of the $C_8$ component outlet of the aromatization unit and the $C_8$ component outlet of the cracking and aromatics conversion unit is in communication with the inlet of the aromatics purification unit, at least one of the $C_4^-$ component outlet of the aromatization unit, the $C_4^-$ component outlet of the cracking and aromatics conversion unit, and the $C_4^-$ component outlet of the aromatics purification unit is in communication with the inlet of the light hydrocarbon conversion unit,
at least one of the $C_5$ component outlet of the aromatization unit, the $C_5$ component outlet of the cracking and aromatics conversion unit, and the $C_5$ component outlet of the aromatics purification unit is in communication with the inlet of the light gasoline blending unit, and the $C_6$-$C_7$ component outlet and the $C_9^+$ component outlet of the cracking and aromatics conversion unit, and optionally at least one of the $C_6$-$C_7$ component outlet and the $C_9^+$ component outlet of the aromatic purification unit, are in communication with the inlet of the cracking and aromatics conversion unit.

12. The method of claim 2, wherein the gasoline fraction used in step 1) has one or more of the following characteristics:
a boiling range of 40-250° C., or a boiling range of 50-200° C.;
an aromatics content of 10 to 100 wt %, or 20 to 80 wt %; and
selected from the group consisting of catalytic cracking gasoline, hydrocracking gasoline, ethylene cracking gasoline, catalytic reformate, straight-run gasoline, LPG or any mixtures thereof, or a partial fraction thereof.

13. The method of claim 2, wherein the aromatization catalyst used in step 1) comprises, based on the weight of the catalyst, 50 to 90 wt % of a molecular sieve selected from aluminosilicates, aluminogallosilicates, aluminosilicophosphates, aluminoferrosilicates having a ten- or twelve-membered ring pore structure, or a combination thereof, and 0.5 to 10 wt % of a modifying metal selected from the group consisting of Group IB, Group IIB, Group VIB, Group VIIB, and Group VIII metals, preferably selected from Zn, Mo, Ga, and Pt,
and/or, the reaction conditions of step 1) include: a reaction temperature of 400-600° C., a reaction pressure of 0.2-3 MPa, and a feeding weight hourly space velocity of 0.5-5 h$^{-1}$.

14. The method of claim 2, wherein the aromatics conversion catalyst used in step 2) comprises an acidic molecular sieve component, an oxide additive, a first metal component immobilized on the acidic molecular sieve component, and a second metal component, wherein the first metal of the first metal component is selected from the group consisting of Group VB metals, Group VIB metals, Group VIIB metals, and combinations thereof, wherein the second metal of the second metal component is a metal different from the first metal, the catalyst has a mediate strong acid content of 0.05-2.0 mmol/g of catalyst, and a ratio of mediate strong acid content to total acid content of 60-99%,
and/or, the reaction conditions of step 2) include: a reaction temperature of 250-500° C., a reaction pressure of 1.5-6.5 MPa, a hydrogen-to-hydrocarbon molar ratio of 1-10, and a feeding weight hourly space velocity of 0.5-5 h$^{-1}$.

15. The method of claim 2, wherein the purifying of step 3) comprises subjecting the $C_8$ component to aromatics extraction separation, non-aromatics selective cracking, or a combination thereof, or
the purifying comprises subjecting the $C_8$ component to extraction separation by extractive distillation using sulfolane solvent; or
the purifying comprises subjecting the $C_8$ component to non-aromatics selective cracking in the presence of a catalyst comprising a molecular sieve component selected from the group consisting of ZSM-5 molecular sieves, MCM-22 molecular sieves, MOR molecular sieves, β molecular sieves, and combinations thereof, and optionally a metal component selected from Group VIB metals, Group VIIB metals, and Group VIII metals;
and/or, the operating conditions for the non-aromatics selective cracking include: a reaction temperature of 300-600° C., a reaction pressure of 0.5-3.0 MPa, a hydrogen-to-hydrocarbon molar ratio of 1-10, and a feeding weight hourly space velocity of 1-15 h$^{-1}$.

16. The method of claim 2, wherein the operating conditions of the steam cracking of step 4) include: a cracking temperature of 600-1000° C., a residence time of 0.01-0.8 s, and a reaction pressure of 0.1-0.3 MPa; or the operating conditions of the dehydrogenation reaction in step 4) include: a reaction temperature of 400-700° C., a weight hourly space velocity of 0.5-10, and a reaction pressure of 0.1-2 MPa.

* * * * *